United States Patent
Okamoto

(10) Patent No.: US 11,638,687 B2
(45) Date of Patent: May 2, 2023

(54) OIL-BASED COSMETIC PREPARATION

(71) Applicant: Shiseido Company, Ltd., Tokyo (JP)

(72) Inventor: Hiroshi Okamoto, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 150 days.

(21) Appl. No.: 17/260,501

(22) PCT Filed: Jul. 19, 2019

(86) PCT No.: PCT/JP2019/028530
§ 371 (c)(1),
(2) Date: Jan. 14, 2021

(87) PCT Pub. No.: WO2020/017650
PCT Pub. Date: Jan. 23, 2020

(65) Prior Publication Data
US 2021/0299030 A1   Sep. 30, 2021

(30) Foreign Application Priority Data
Jul. 19, 2018 (JP) .............................. JP2018-136248

(51) Int. Cl.
*A61K 8/25* (2006.01)
*A61K 8/37* (2006.01)
*A61K 8/73* (2006.01)
*A61K 8/81* (2006.01)
*A61K 8/891* (2006.01)
*A61Q 1/02* (2006.01)
*A61Q 1/04* (2006.01)
*A61Q 1/10* (2006.01)

(52) U.S. Cl.
CPC ............... *A61K 8/891* (2013.01); *A61K 8/25* (2013.01); *A61K 8/37* (2013.01); *A61K 8/375* (2013.01); *A61K 8/732* (2013.01); *A61K 8/8152* (2013.01); *A61Q 1/04* (2013.01)

(58) Field of Classification Search
None
See application file for complete search history.

(56) References Cited

U.S. PATENT DOCUMENTS

2019/0201317 A1\*   7/2019   Konishi ................. A61K 8/898

FOREIGN PATENT DOCUMENTS

| JP | 2000-281532 A | 10/2000 | |
|---|---|---|---|
| JP | 2002-154918 A | 5/2002 | |
| JP | 2007-023022 A | 2/2007 | |
| JP | 2009-132638 A | 6/2009 | |
| JP | 2009-203212 A | 9/2009 | |
| JP | 2009-263329 A | 11/2009 | |
| JP | 2016-166146 A | 9/2016 | |
| JP | 2016-166147 A | 9/2016 | |
| JP | 2017-178839 A | 10/2017 | |
| WO | WO-2018/008238 A1 | 1/2018 | |
| WO | WO-2018008238 A1 \* | 1/2018 | ............ A61K 8/898 |

\* cited by examiner

*Primary Examiner* — Brian Gulledge
(74) *Attorney, Agent, or Firm* — Foley & Lardner LLP

(57) ABSTRACT

The present invention provides an oil-based cosmetic which is excellent in terms of a matte texture, while being highly stable. An oil-based cosmetic which is characterized by containing the following components (a)-(e).
(a) a crosslinked organopolysiloxane
(b) an amorphous anhydrous silicic acid
(c) an oil-based gelling agent having a sugar skeleton
(d) a liquid oil
(e) a powder.

5 Claims, No Drawings

OIL-BASED COSMETIC PREPARATION

CROSS-REFERENCE TO RELATED APPLICATIONS

This application is the U.S. National Stage of PCT/JP2019/028530, filed Jul. 19, 2019, which claims priority to JP 2018-136248, filed Jul. 19, 2018.

FIELD OF THE INVENTION

The present invention relates to an oil-based cosmetic, and in particular to an oil-based cosmetic having a matte texture and good stability.

BACKGROUND OF THE INVENTION

The texture of the skin and lips to which a cosmetic has been applied is roughly classified into two: one which provides a glossy texture and the other one which provides a matte texture. Regarding them, an oily solid cosmetic material containing a partially crosslinked organopolysiloxane and solid oil and/or semi-solid oil is known (see Patent Literature 1). However, its matte texture needs to be improved.

An oil-based cosmetic containing a crosslinked organopolysiloxane and an amorphous silicic anhydride is also known (see Patent Literature 2). However, the matte texture and stability thereof need to be improved.

CITATION LIST

Patent Literature

[Patent Literature 1] Japanese Unexamined Patent Application No. 2000-281532
[Patent Literature 2] Japanese Unexamined Patent Application No. 2002-154918

DISCLOSURE OF THE INVENTION

Problem to be Solved by the Invention

The present invention has been made in view of the conventional art, and an object thereof is to provide an oil-based cosmetic having a matte texture and good stability.

Means to Solve the Problem

The present inventors have conducted intensive studies to solve the problem and as a result have found that an excellent matte texture and good stability can be obtained by an oil-based cosmetic containing a specific amount of (a) a crosslinked organopolysiloxane, (b) an amorphous silicic anhydride, (c) an oil-based gelling agent having a sugar skeleton, (d) a liquid oil and (e) a powder.

Accordingly, the oil-based cosmetic according to the present invention comprises the following components (a) to (e):
   (a) a crosslinked organopolysiloxane;
   (b) an amorphous silicic anhydride;
   (c) an oil-based gelling agent having a sugar skeleton;
   (d) a liquid oil; and
   (e) a powder.

In the oil-based cosmetic, the content of the oil-based gelling agent having a sugar skeleton (c) is preferably 1 to 15% by mass.

In the oil-based cosmetic, the liquid oil (d) preferably includes a silicone oil and a polar oil.

A lip cosmetic according to the present invention is characterized by comprising the oil-based cosmetic.

Effect of the Invention

The present invention can provide an oil-based cosmetic having a matte texture and good stability.

BEST MODE FOR CARRYING OUT THE INVENTION

Hereinafter, embodiments of the present invention will be described in detail.

The oil-based cosmetic according to the present invention comprises the following components (a) to (e):
   (a) a crosslinked organopolysiloxane;
   (b) an amorphous silicic anhydride;
   (c) an oil-based gelling agent having a sugar skeleton;
   (d) a liquid oil; and
   (e) a powder.

((a) Crosslinked Organopolysiloxane)

A crosslinked organopolysiloxane obtained by addition reaction and crosslinking reaction of (a) an organopolysiloxane having at least two lower alkenyl groups per molecule and (b) an organopolysiloxane having at least two hydrogen atoms bonded to a silicon atom per molecule in the presence of a platinum catalyst may be used as the crosslinked organopolysiloxane.

Crosslinked organopolysiloxanes described below may also be used.

(1) A crosslinked organopolysiloxane containing at least a $R_2SiO$ unit, a $RSiO_{1.5}$ unit and a $R_3SiO_{0.5}$ unit out of a $R_2SiO$ unit, a $RSiO_{1.5}$ unit, a $R_3SiO_{0.5}$ unit and a $SiO_2$ unit, in which each R independently represents a hydrogen atom, an alkyl group such as a methyl group, an ethyl group and a propyl group, or an aryl group such as a phenyl group and a trimethyl group, or an unsaturated aliphatic group such as a vinyl group, or the like, and the weight ratio of the $R_2SiO$ unit to the $RSiO_{1.5}$ unit is in the range of 1 to 30:1.

(2) A crosslinked organohydropolysiloxane obtained by addition of (c) an organohydropolysiloxane and (d) an organopolysiloxane having an unsaturated aliphatic group, in which the amount of hydrogen or the unsaturated aliphatic group in (c) and (d) is in the range of 1 to 20% by mole when the organopolysiloxane is acyclic, and in the range of 1 to 50% by mole when the organopolysiloxane is cyclic.

A crosslinked alkyl aryl polysiloxane and a crosslinked alkyl polysiloxane are preferably used as the crosslinked organopolysiloxane. Examples of crosslinked alkyl aryl polysiloxanes include a crosslinked organopolysiloxane having an alkyl group having 1 to 5 carbon atoms and an aryl group having 6 to 10 carbon atoms. Specific examples thereof include methylphenyl polysiloxane and ethylphenyl polysiloxane.

Examples of crosslinked alkyl polysiloxanes include crosslinked monoalkyl polysiloxane and crosslinked dialkyl polysiloxane having an alkyl group having 1 to 5 carbon atoms. Specific examples thereof include crosslinked monomethyl polysiloxane, crosslinked dimethyl polysiloxane, crosslinked monoethyl polysiloxane, crosslinked diethyl polysiloxane and crosslinked methylethyl polysiloxane.

Examples of commercially available crosslinked alkyl polysiloxanes include Dow Corning 9041 Silicone Elastomer Blend (made by Dow Corning Toray Silicone, Co. Ltd.), which is a mixture of dimethyl polysiloxane and partially crosslinked silicone (concentration: 16% by weight), KSG15 in the form of paste (made by Shin-Etsu Chemical Co., Ltd.), which is a mixture of decamethylcyclopentasiloxane and crosslinked methyl polysiloxane (concentration: 5% by weight), KSG16 in the form of paste (made by Shin-Etsu Chemical Co., Ltd.), which is a mixture of low viscosity dimethyl polysiloxane and crosslinked methyl polysiloxane (concentration: 20 to 30% by weight), and KSG18 in the form of paste (made by Shin-Etsu Chemical Co., Ltd.), which is a mixture of methylphenyl polysiloxane and crosslinked methylphenyl polysiloxane (concentration: 10 to 20% by weight). One or two or more of these crosslinked organopolysiloxanes may be used.

In the present invention, the content of the crosslinked organopolysiloxane is preferably 1 to 10% by mass in pure content based on the total amount of the oil-based cosmetic. The content is more preferably 3% by mass or more. When the content is less than 1% by mass, a sufficient matte texture cannot be obtained.

Furthermore, the content is more preferably 8% by mass or less. When the content is more than 10% by mass, the smoothness in application may be reduced.

((b) Amorphous Silicic Anhydride)

Examples of amorphous silicic anhydrides include a hydrophilic amorphous silicic anhydride prepared by hydrolyzing silicon tetrachloride in hydrogen/oxygen flame, and an amorphous silicic anhydride prepared by hydrophobizing the surface of the hydrophilic amorphous silicic anhydride. The amorphous silicic anhydride may be a hydrophilic amorphous silicic anhydride or a hydrophobized amorphous silicic anhydride. Examples of methods of the hydrophobization include trimethylsiloxylation using trimethylsilyl chloride, hexamethyldisilazane and the like, methylation using dimethyldichlorosilane, baking of coating using methyl hydrogen polysiloxane, and coating using dimethyl polysiloxane, metal soap and the like. One or two or more of these amorphous silicic anhydrides may be used.

An amorphous silicic anhydride has an average particle size of preferably 0.001 to 0.05 μm, and more preferably 0.001 to 0.02 μm. When the average particle size is in that range, good feeling on use without friction and good stability without separation of oil components can be achieved. The average particle size of the amorphous silicic anhydride may be measured by using a transmission electron microscope.

Examples of commercially available amorphous silicic anhydrides include Aerosil 200 (made by NIPPON AEROSIL), Aerosil 300 (made by NIPPON AEROSIL), Aerosil R972 (made by NIPPON AEROSIL), Aerosil R974 (made by NIPPON AEROSIL), Aerosil R202 (made by NIPPON AEROSIL), Aerosil RY200 (made by NIPPON AEROSIL) and Taranox 500 (made by Tarco Inc.).

The content of an amorphous silicic anhydride is preferably 0.1 to 10% by mass based on the total amount of the oil-based cosmetic. The content is more preferably 0.5% by mass or more. When the content is less than 0.1% by mass, a sufficient matte texture cannot be obtained.

Furthermore, the content is more preferably 7% by mass or less. When the content is more than 5% by mass, smoothness in application may be reduced.

((c) Oil-Based Gelling Agent Having Sugar Skeleton)

Any material may be used as the oil-based gelling agent having a sugar skeleton as long as it can usually be used for cosmetics. Specific examples thereof include sugar fatty acid esters such as dextrin fatty acid ester, fructooligosaccharide fatty acid ester and sucrose fatty acid ester.

Although the cosmetics thickened by the component (a) and the component (b) have drawbacks in that oil separation is likely to occur, an oil-based cosmetic having excellent stability and high temperature stability can be obtained by containing the oil-based gelling agent having a sugar skeleton of the present invention.

Examples of sugars constituting the oil-based gelling agent having a sugar skeleton of the present invention include sugars and alkyl sugars, and monosaccharide and polysaccharide may be used. Monosaccharide, oligosaccharide and polysaccharide are not particularly limited, and examples thereof include glucose, galactose, fructose, mannose, sucrose, lactose, maltose, trehalose, melibiose, raffinose, fructooligosaccharide, dextrin and inulin. An ester compound prepared by the reaction of such a sugar or an alkyl sugar with a fatty acid is preferably used as the oil-based gelling agent.

A linear or branched, saturated or unsaturated fatty acid having 6 to 32 carbon atoms is preferred as a fatty acid, and those having 8 to 24 carbon atoms are more preferred. Examples of fatty acids include caprylic acid, capric acid, lauric acid, myristic acid, palmitic acid, stearic acid, arachidic acid, behenic acid, oleic acid, linoleic acid, linolenic acid, arachidonic acid, 2-ethylhexanoic acid, isomyristic acid, isopalmitic acid, isostearic acid and octyldodecanoic acid.

Examples of preferred oil-based gelling agents having a sugar skeleton comprising a fatty acid ester include dextrin fatty acid ester and sucrose fatty acid ester.

An ester of a linear or branched, saturated or unsaturated fatty acid having 6 to 32 carbon atoms and dextrin, which has an average degree of substitution of 2.5 or more per monosaccharide is preferred as dextrin fatty acid ester.

Specific examples thereof include dextrin palmitate, dextrin (palmitate/ethylhexanoate), dextrin myristate, dextrin stearate, dextrin palmitate/stearate, dextrin oleate, dextrin isopalmitate and dextrin isostearate.

Examples of commercially available products of dextrin palmitate include Rheopearl KL2, Rheopearl TL2 (both made by Chiba Flour Milling Co., Ltd.); examples of dextrin (palmitate/ethylhexanoate) include Rheopearl TT2 (made by Chiba Flour Milling Co., Ltd.); and examples of dextrin myristate include Rheopearl MKL2 (made by Chiba Flour Milling Co., Ltd.).

An ester of a linear or branched, saturated or unsaturated fatty acid having 6 to 32 carbon atoms and sucrose, which has an average degree of substitution of 2.5 or more is preferred as sucrose fatty acid ester.

The content of the oil-based gelling agent having a sugar skeleton is preferably 1 to 15% by mass based on the total amount of the oil-based cosmetic. When the content of the oil-based gelling agent is 1 to 15% by mass, an oil-based cosmetic in the form of paste having a matte texture, smoothness in application and good high temperature stability can be obtained. The content is more preferably 3% by mass or more. When the content is less than 1% by mass, a matte texture and stability are poor.

Furthermore, the content is more preferably less than 8% by mass. When the content is more than 15% by mass, smoothness in application may be reduced or the cosmetic may have an oily texture.

((d) Liquid Oil)

A liquid oil usually used for cosmetics may be used as the liquid oil.

A silicone oil and a polar oil are preferably contained as the liquid oil of the present invention.

Examples of silicone oils include non-volatile silicone oils such as dimethyl polysiloxane, phenyl trimethicone, diphenyl dimethicone, diphenyl siloxyphenyl trimethicone and trimethyl pentaphenyl trisiloxane, which have a polymerization degree of 6 or more, and volatile silicone oils such as dimethyl polysiloxane, decamethyl cyclopentasiloxane, octamethyl cyclotetrasiloxane, dodecamethyl cyclohexasiloxane, methyl trimethicone, dimethyl polysiloxane, decamethyl tetrasiloxane and ethyl trisiloxane, which have a polymerization degree of 2 to 5.

Examples of polar oils include glyceryl tri-2-ethylhexanoate, diisostearyl malate, glyceryl diisostearate, diglyceryl triisostearate, glyceryl tri(caprylate/caprate), neopentyl glycol dicaprate, pentaerythrityl tetra-2-ethylhexanoate, diethylhexyl sebacate, octyl dodecanol, trimethylolpropane tri-2-ethylhexanoate, oxystearyl oxystearate, pentaerythrityl tetra (ethylhexanate/benzoate), trioctanoin, pentaerythrityl tetraoctanoate, dipentaerythrityl hexahydroxystearate, castor oil, diisopropyl sebacate, pentaerythritol tetraoctanoate and trimethylolpropane triisostearate.

Examples of non-volatile liquid oils other than silicone oils or polar oils include hydrocarbon oils, natural animal and vegetable oils and semi-synthetic oils.

Examples of hydrocarbon oils include hydrogenated polyisobutene, liquid paraffin, squalane, squalene, heavy liquid isoparaffin, polyisobutylene and α-olefin oligomer.

Examples of natural animal and vegetable oils and semi-synthetic oils include avocado oil, linseed oil, almond oil, olive oil, kaya oil, cod liver oil, apricot kernel oil, wheat germ oil, sesame oil, rice germ oil, rice bran oil, sasanqua oil, safflower oil, Chinese paulownia oil, cinnamon oil, turtle oil, soy bean oil, tea seed oil, camellia oil, evening primrose oil, corn oil, rapeseed oil, Japanese tung oil, germ oil, persic oil, palm oil, red palm oil, palm kernel oil, castor oil, sunflower oil, grape oil, jojoba oil, macadamia nut oil, cotton seed oil, coconut oil, coconut fatty acid triglyceride, peanut oil, liquid lanolin, reduced lanolin, lanolin alcohol, lanolin acetate, lanolin fatty acid isopropyl ester, POE lanolin alcohol ether, POE lanolin alcohol acetate, lanolin fatty acid polyethylene glycol, POE hydrogenated lanolin alcohol ether and egg yolk oil.

Examples of volatile oils other than volatile silicone oil include light liquid isoparaffin.

The content of liquid oil is preferably 40 to 90% by mass based on the total amount of the oil-based cosmetic. The content is more preferably 50% by mass or more. When the content is less than 40% by mass, moist feeling is insufficient.

The content is more preferably less than 80% by mass. When the content is more than 90% by mass, a matte texture is insufficient.

((e) Powder)

Any powder may be used without particular limitation as long as it is usually used for cosmetics.

Examples of powders include a spherical powder, a plate-like powder and a color material.

Any spherical powder may be used in the present invention without particular limitation as long as it is usually used for oil-based cosmetics.

Examples of spherical powders include spherical resin powders such as methyl polymethacrylate, organopolysiloxane elastomer, polystyrene, a polyamide resin (nylon), polyethylene, a copolymer of styrene and acrylic acid, a benzoguanamine resin, polytetrafluoroethylene and a silicone resin.

The powder of the present invention may also include a plate-like powder. The ratio of the minor diameter to the major diameter of the plate-like powder is preferably 1 to 10 or more.

Examples of plate-like powders include inorganic powders such as mica, synthetic mica, talc, sericite, aluminum oxide, magnesium oxide, zirconium oxide, magnesium carbonate, calcium carbonate, calcium sulfate, chromium oxide, chromium hydroxide, aluminum silicate, magnesium silicate, aluminum magnesium silicate, kaolin, silicon carbide, barium sulfate, bentonite, smectite and boron nitride, organic powders such as N-acyl lysine, and composite powders such as fine particulate titanium oxide-coated mica titanium, fine particulate zinc oxide-coated mica titanium and barium sulfate-coated mica titanium.

A color material may also be contained in the cosmetics according to the present invention. The color material is contained for the purpose of coloring the formulation. A color material usually contained in an oil-based cosmetic, such as a pigment, a pearl pigment and those prepared by insolubilizing them may be used as the color material.

Examples of color materials include inorganic white pigments (titanium dioxide and zinc oxide), inorganic red pigments (iron oxide (red iron oxide) and iron titanate), inorganic brown pigments (γ-iron oxide), inorganic yellow pigments (yellow iron oxide and ocher), inorganic black pigments (black iron oxide, carbon, and lower titanium dioxide), inorganic purple pigments (manganese violet and cobalt violet), inorganic green pigments (chromium oxide, chromium hydroxide, and cobalt titanate), inorganic blue pigments (ultramarine and iron blue), pearl pigments (titanium oxide-coated mica, titanium oxide-coated bismuth oxychloride, titanium oxide-coated talc, colored titanium oxide-coated mica, bismuth oxychloride, and fish scale guanine), metal powder pigments (aluminum powder and copper powder), organic pigments (Red No. 202, Red No. 205, Red No. 220, Red No. 228, Red No. 405, Orange No. 203, Orange No. 204, Yellow No. 205, Yellow No. 401, and Blue No. 404), organic pigments such as zirconium, barium or aluminum lake (Red No. 3, Red No. 104, Red No. 227, Red No. 401, Orange No. 205, Yellow No. 4, Yellow No. 202, Green No. 3, and Blue No. 1), natural pigments (chlorophyll, carotenoid (β-carotene), carthamin, cochineal, chalcone, curcumin, betanin, flavonol, flavone, anthocyanidin, anthraquinone, and naphthoquinone), and functional pigments (boron nitride, photochromic pigment, synthetic fluorophlogopite, iron-containing synthetic fluorophlogopite, and hybrid fine powder).

The content of powder is preferably 0.1 to 40% by mass based on the total amount of the oil-based cosmetic. The content is more preferably 5% by mass or more, and further preferably 8% by mass or more. When the content is less than 0.1% by mass, a sufficient matte texture may not be obtained.

Furthermore, the content is more preferably 38% by mass or less, and further preferably 30% by mass or less because the cosmetic becomes smoother. When the content is more than 40% by mass, smooth feeling in application may be reduced.

Components usually used for cosmetics, such as a semi-solid oil, a solid oil, a surfactant, a film forming agent, a moisturizer, an ultraviolet absorber, a beauty component, a fiber and a flavoring agent may be contained in the oil-based cosmetic according to the present invention in addition to the essential components within the range that the effect of the present invention is not reduced.

Examples of semi-solid oils include vaseline, pentaerythritol tetra(behenate/benzoate/ethylhexanoate), dipentaerythrityl hexahydroxystearate, dimer dilinoleate, macadamia nut oil polyglyceryl-6 esters behenate, dipentaerythrityl tetra (hydroxystearate/isostearate) and bis-diglyceryl polyacyl adipate-2.

The content of the semi-solid oil is preferably 30% by mass or less. When the semi-solid oil is contained, stability and high temperature stability of the oil-based cosmetic can be improved.

Examples of solid oils include solid oils and fats, waxes, solid hydrocarbons and higher alcohols. Specific examples thereof include solid oils and fats such as cacao butter and hydrogenated castor oil; waxes such as Japan wax, carnauba wax, beeswax, white beeswax, candelilla wax and jojoba wax; hydrocarbon waxes such as polyethylene wax, paraffin wax, ceresin and microcrystalline wax; higher alcohols such as cetyl alcohol, stearyl alcohol, behenyl alcohol and batyl alcohol; and silicone wax.

The content of solid oil is preferably 10% by mass or less. When the solid oil is contained, stability and high temperature stability of the oil-based cosmetic can be improved.

Examples of nonionic surfactants include polyoxyethylene surfactants such as polyoxyethylene alkyl ether, polyoxyethylene fatty acid ester, polyoxyethylene polyhydric alcohol fatty acid partial ester and polyoxyethylene hydrogenated castor oil derivatives, alkyl polyglycosides such as octyl polyglycoside, polygrycerol surfactants such as polyglycerol fatty acid ester and polyglycerol alkyl ether, sugar alcohol hydroxyalkyl ethers such as maltitol hydroxyalkyl ether and fatty acid diethanolamide.

Furthermore, an anionic surfactant such as higher fatty acid salts, alkyl benzene sulfonates, phosphates, alkyl sulfates, alkyl sulfate esters and polyoxyethylene alkyl sulfate esters, a cationic surfactant such as amino acids, alkyl trimethyl ammonium salts, dialkyl dimethyl ammonium salts and alkyl dimethylamine oxides, and other surfactants may also be contained.

Examples of film forming agents include siliconized pullulan, trimethylsiloxysilicic acid, dimethylaminomethacrylate quaternized salt, a vinyl pyrrolidone N,N-dimethylethylammonioethyl methacrylate salt copolymer, a silicone/polyether polyurethane resin, a (methacryloyloxyethylcarboxybetaine/methacrylicalkyl) copolymer, dextrin, a (vinyl pyrrolidone/VA) copolymer, alkyl acrylate copolymer ammonium, polyvinyl alcohol, polyethyl acrylate, a (alkyl acrylate/octyl acrylamide) copolymer, a (acrylate/propyl trimethicone methacrylate) copolymer, polyvinyl acetate, a (alkyl acrylate/dimethicone) copolymer, polyether grafted acrylic silicone, trimethylsiloxysilicic acid and a fluoro-modified silicone resin.

Examples of the moisturizing agent include dipropylene glycol, polyethylene glycol, propylene glycol, glycerin, 1,3-butylene glycol, xylitol, sorbitol, maltitol, chondroitin sulfate, hyaluronic acid, mucoitin sulfate, caronic acid, atelocollagen, cholesteryl-12-hydroxystearate, sodium lactate, bile acid salt, dl-pyrrolidone carboxylate, short-chain soluble collagen, diglycerin (EO) PO adducts, *Rosa roxburghii* fruit extracts, *Achillea millefolium* extracts, and melilot extracts.

Examples of the ultraviolet absorber include benzoic acid ultraviolet absorbers (e.g., p-aminobenzoic acid (hereinafter, abbreviated to PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid ultraviolet absorbers (e.g., homomenthyl-N-acetyl anthranilate); salicylic acid ultraviolet absorbers (e.g., amyl salicylate, menthyl salicylate, homomenthyl salicylate, octyl salicylate, phenyl salicylate, benzyl salicylate, and p-isopropanolphenyl salicylate); cinnamic acid ultraviolet absorbers (e.g., octylmethoxy cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-di-p-methoxy cinnamate); benzophenone ultraviolet absorbers (e.g., 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-t-octylphenyl) benzotriazole; 2-(2'-hydroxy-5'-methylphenylbenzotriazole); dibenzalazine; dianisoylmethane; 4-methoxy-4'-t-butyldibenzoylmethane; 5-(3,3-dimethyl-2-norbornylidene)-3-pentan-2-one.

Examples of other components that may be blended include antiseptics (ethylparaben, butylparaben, etc.); skin-lightening agents (e.g., placenta extracts, *Saxifraga stolonifera* extracts, and arbutin); blood flow stimulants (e.g., nicotinic acid, nicotinic acid benzyl ester, tocopherol nicotinate, nicotinic acid β-butoxy ethyl ester, minoxidil or minoxidil analog, Vitamin E, γ-oryzanol, alkoxycarbonylpyridine N-oxide, carpronium chloride, and acethylcholine or acetylcholine derivatives); various extracts (e.g., ginger, phellodendron bark, coptis rhizome, lithospermum root, birch, loquat, carrot, aloe, mallow, iris, grape, luffa, capsicum, citrus unshiu peel, Japanese angelica root, peony and algae), activators (e.g., pantothenyl ethyl ether, nicotinamide, biotin, pantothenic acid, royal jelly, and cholesterol derivatives); and anti-seborrheic agents (e.g., piridoxines and thianthol).

The oil-based cosmetic of the present invention may be in the form of, for example, lip cosmetics such as a lip gloss, a lip primer, a topcoat for lipsticks and a lip balm, eye shadow and foundation. Of them, lip cosmetics are preferred.

Examples

The present invention will be described in more detail with reference to Examples below, but the present invention is not limited thereto. The content of the component is represented by % by mass based on the amount of the system in which the component is contained unless otherwise specified.

Before describing Examples, the test method for evaluation used in the present invention will be described.

Evaluation (1): Matte Texture when Finished

Ten expert panelists applied the sample to their lips and evaluated a matte texture when finished and smoothness in application. They evaluated the sample in comparison with a standard product.

Matte texture when finished: 1 (none)←2 (little)←3 (moderate)→4 (slightly matte)→5 (matte)
  A: Average score of 4.5 or more
  B: Average score of 3.5 or more and less than 4.5
  C: Average score of 2.5 or more and less than 3.5
  D: Average score of 1.5 or more and less than 2.5
  E: Average score of less than 1.5
Evaluation (2): Stability 10 g of the sample was heated and put in transparent plastic pot 3-100 (50 ml) (made by Shinto Kagaku Co., Ltd.), and after the sample was solidified, the plastic pot was horizontally fixed, and the stability of the sample after being stored for 24 hours at 25° C. or 37° C. (no leakage of oil) was evaluated.
  A: No leakage of oil at all.
  B: Oil leakage occurred.
  C: Oil leakage occurred, so that oil reached the upper side of the pot.
  D: Oil leakage occurred, so that oil leaked out of the pot.

The present inventors produced the oil-based cosmetics (lip glosses) shown in the following Table 1 by a conventional method, and performed measurements based on the evaluation method. The results are shown in Table 1.

TABLE 1

| | | Test Example | | | | | | | | |
|---|---|---|---|---|---|---|---|---|---|---|
| | | 1-1 | 1-2 | 1-3 | 1-4 | 1-5 | 1-6 | 1-7 | 1-8 | 1-9 |
| (a) | Partially crosslinked silicone swollen composition (*1) | 30.00% (Pure content 4.8%) | 30.00% (Pure content 4.8%) | 30.00% (Pure content 4.8%) | 30.00% (Pure content 4.8%) | 30.00% (Pure content 4.8%) | 30.00% (Pure content 4.8%) | 30.00% (Pure content 4.8%) | 30.00% (Pure content 4.8%) | 30.00% (Pure content 4.8%) |
| (b) | Silica dimethyl silylate (*2) | 3.50% | 3.50% | 3.50% | 3.50% | 3.50% | 3.50% | 3.50% | 3.50% | 3.50% |
| (c) | Dextrin palmitate | — | 1.00% | 5.00% | 10.00% | 10.00% | — | — | — | — |
| | Dextrin (palmitate/ethyl hexanoate) | — | — | — | — | — | 1.00% | 5.00% | 10.00% | 15.00% |
| (d) | Dimethyl polysiloxane | 18.50% | 18.50% | 18.50% | 18.50% | 18.50% | 18.50% | 18.50% | 18.50% | 18.50% |
| | Glyceryl tri-2-ethylhexanoate | 20.00% | 19.00% | 15.00% | 10.00% | 10.00% | 19.00% | 15.00% | 10.00% | 5.00% |
| | Diisostearyl malate | 7.20% | 7.20% | 7.20% | 7.20% | 7.20% | 7.20% | 7.20% | 7.20% | 7.20% |
| | Glyceryl diisostearate | 3.60% | 3.60% | 3.60% | 3.60% | 3.60% | 3.60% | 3.60% | 3.60% | 3.60% |
| (e) | Polymethyl methacrylate | 10.00% | 10.00% | 10.00% | 10.00% | — | 10.00% | 10.00% | 10.00% | 10.00% |
| | Mica | — | — | — | — | 10.00% | — | — | — | — |
| | Color material | 7.20% | 7.20% | 7.20% | 7.20% | 7.20% | 7.20% | 7.20% | 7.20% | 7.20% |
| Matte finish after applying | | (Standard) | C | B | A | A | C | B | A | A |
| Stability (25° C.) | | D | B | A | A | A | B | A | A | A |
| Stability (37° C.) | | D | B | A | A | A | B | B | A | A |

(*1) Composition of partially crosslinked silicone swollen in dimethyl polysiloxane: Dow Corning 9041 Silicone Elastomer Blend (made by Dow Corning Toray Silicone, Co Ltd.)
Partially crosslinked silicone:dimethyl polysiloxane = 16:84 (wt/wt)
(*2) AEROSIL R972 (made by NIPPON AEROSIL Co., Ltd.)

Table 1 shows that a matte texture and stability can be improved when an oil-based gelling agent having a sugar skeleton is contained in an oil-based cosmetic containing a crosslinked organopolysiloxane and an amorphous silicic anhydride.

Table 1 also shows that a cosmetic having excellent high temperature stability can be obtained when the content of the oil-based gelling agent having a sugar skeleton is increased.

Next the present inventors evaluated compositions in which the content of the crosslinked organopolysiloxane (a), the amorphous silicic anhydride (b) and the powder (e) was changed. The method of evaluation is the same as the above method shown in Table 1.

The results are shown in Table 2 to 4.

TABLE 2

| | | Text Example | | | | |
|---|---|---|---|---|---|---|
| | | 2-1 | 2-2 | 2-3 | 1-3 | 2-4 |
| (a) | Partially crosslinked silicone swolllen composition (*1) | 0% (Pure content 0%) | 6.25% (Pure content 1%) | 18.75% (Pure content 3%) | 30% (Pure content 4.8%) | 43.75% (Pure content 7%) |

TABLE 2-continued

|  |  | Text Example | | | | |
|---|---|---|---|---|---|---|
|  |  | 2-1 | 2-2 | 2-3 | 1-3 | 2-4 |
| (b) | Silica dimethyl silyate (*2) | 3.50% | 3.50% | 3.50% | 3.50% | 3.50% |
| (c) | Dextrin palmitate (*3) | 5.00% | 5.00% | 5.00% | 5.00% | 5.00% |
| (d) | Dimethyl polysiloxane (*5) | 48.50% | 42.25% | 29.75% | 18.50% | 4.75% |
|  | Glyceryl tri-2-ethylhexanoate | 15.00% | 15.00% | 15.00% | 15.00% | 15.00% |
|  | Diisostearyl malate | 7.20% | 7.20% | 7.20% | 7.20% | 7.20% |
|  | Glyceryl diisostearate | 3.60% | 3.60% | 3.60% | 3.60% | 3.60% |
| (e) | Polymethyl methacrylate | 10.00% | 10.00% | 10.00% | 10.00% | 10.00% |
|  | Color material | 7.20% | 7.20% | 7.20% | 7.20% | 7.20% |
|  | Matte finish after applying | D | D | C | B | A |
|  | Stability (25° C.) | D | C | B | A | A |
|  | Stability (37° C.) | D | C | B | A | A |

Table 2 shows that the effect of the present invention, i.e., a matte texture and stability, cannot be obtained when the crosslinked organopolysiloxane (a) is not used.

TABLE 3

|  |  | Text Example | | | | | |
|---|---|---|---|---|---|---|---|
|  |  | 3-1 | 3-2 | 3-3 | 1-3 | 3-4 | 3-5 |
| (a) | Partially crosslinked silicone swolllen composition (*1) | 30% (Pure content 4.8%) | 30% (Pure content 4.8%) | 30% (Pure content 4.8%) | 30% (Pure content 4.8%) | 30% (Pure content 4.8%) | 30% (Pure content 4.8%) |
| (b) | Silica dimethyl silyate (*2) | 0.00% | 0.50% | 1.00% | 3.50% | 5.00% | 7.00% |
| (c) | Dextrin palmitate (*3) | 5.00% | 5.00% | 5.00% | 5.00% | 5.00% | 5.00% |
| (d) | Dimethyl polysiloxane (*5) | 18.50% | 18.50% | 18.50% | 18.50% | 18.50% | 18.50% |
|  | Glyceryl tri-2-ethylhexanoate | 18.50% | 18.00% | 17.50% | 15.00% | 13.50% | 11.50% |
|  | Diisostearyl malate | 7.20% | 7.20% | 7.20% | 7.20% | 7.20% | 7.20% |
|  | Glyceryl diisostearate | 3.60% | 3.60% | 3.60% | 3.60% | 3.60% | 3.60% |
| (e) | Polymethyl methacrylate | 10.00% | 10.00% | 10.00% | 10.00% | 10.00% | 10.00% |
|  | Color material | 7.20% | 7.20% | 7.20% | 7.20% | 7.20% | 7.20% |
|  | Matte finish after applying | D | C | B | B | B | A |
|  | Stability (25° C.) | C | B | B | A | A | A |
|  | Stability (37° C.) | C | C | B | A | A | A |

Table 3 shows that when the amorphous silicic anhydride (b) is contained, a matte texture can be felt and stability is further improved.

Table 4 shows that a matte texture is particularly improved when the total amount of the powder (e) is increased.

According to the results of the above studies by the present inventors, the oil-based cosmetic according to the present invention comprises (a) a crosslinked organopoly-

TABLE 4

|  |  | Text Example | | | | | |
|---|---|---|---|---|---|---|---|
|  |  | 4-1 | 4-2 | 4-3 | 1-3 | 4-4 | 4-5 |
| (a) | Partially crosslinked silicone swolllen composition (*1) | 30% (Pure content 4.8%) | 30% (Pure content 4.8%) | 30% (Pure content 4.8%) | 30% (Pure content 4.8%) | 30% (Pure content 4.8%) | 30% (Pure content 4.8%) |
| (b) | Silica dimethyl silyate (*2) | 3.50% | 3.50% | 3.50% | 3.50% | 3.50% | 3.50% |
| (c) | Dextrin palmitate (*3) | 5.00% | 5.00% | 5.00% | 5.00% | 5.00% | 5.00% |
| (d) | Dimethyl polysiloxane (*5) | 18.50% | 18.50% | 18.50% | 18.50% | 18.50% | 13.50% |
|  | Glyceryl tri-2-ethylhexanoate | 25.00% | 24.00% | 20.00% | 15.00% | 5.00% | 0.00% |
|  | Diisostearyl malate | 7.20% | 7.20% | 7.20% | 7.20% | 7.20% | 7.20% |
|  | Glyceryl diisostearate | 3.60% | 3.60% | 3.60% | 3.60% | 3.60% | 3.60% |
| (e) | Polymethyl methacrylate | 0.00% | 1.00% | 5.00% | 10.00% | 20.00% | 30.00% |
|  | Color material | 7.20% | 7.20% | 7.20% | 7.20% | 7.20% | 7.20% |
|  | Matte finish after applying | D | C | B | B | A | A |
|  | Stability (25° C.) | B | A | A | A | A | A |
|  | Stability (37° C.) | B | B | A | A | A | A | siloxane, (b) an amorphous silicic anhydride, (c) an oil-based gelling agent having a sugar skeleton, (d) a liquid oil and (e) a powder.

Formulation Examples of the oil-based cosmetic according to the present invention will be described below. The present invention is not limited to any of these Formulation Examples and is specified by the claims.

Formulation Example 1: Lip Gloss

| Component | Blending amount (by mass) |
| --- | --- |
| Partially crosslinked silicone swollen composition (*1) | 30.00% |
| Silica dimethyl silylate (*2) | 3.50% |
| Dextrin palmitate | 5.00% |
| Dimethyl polysiloxane | 18.50% |
| Glyceryl tri-2-ethylhexanoate | 15.00% |
| Diisostearyl malate | 7.20% |
| Glyceryl diisostearate | 3.60% |
| Polymethyl methacrylate | 10.00% |
| Color material | 7.20% |

Formulation Component 2: Eye Shadow

| Component | Blending amount (by mass) |
| --- | --- |
| Partially crosslinked silicone swollen composition (*1) | 30.00% |
| Silica dimethyl silylate (*2) | 3.50% |
| Dextrin palmitate | 5.00% |
| Triethylhexanoin | 16.5% |
| Hydrogenated polydecene | 15.0% |
| Mica | 18.6% |
| Iron oxide | 10.5% |
| Titanium oxide | 0.9% |

What is claimed is:

1. An oil-based cosmetic comprising the following components (a) to (e):
    (a) 3 to 7% by mass of a crosslinked organopolysiloxane;
    (b) an amorphous silicic anhydride;
    (c) 1 to less than 8% by mass of an oil-based gelling agent having a sugar skeleton;
    (d) a liquid oil; and
    (e) 8 to 38% by mass of a powder.

2. The oil-based cosmetic according to claim 1, wherein the liquid oil (d) comprises a silicone oil and a polar oil.

3. The oil-based cosmetic according to claim 1, wherein a content of the amorphous silicic anhydride (b) is 0.5 to 7% by mass.

4. A lip cosmetic comprising the oil-based cosmetic according to claim 1.

5. A lip cosmetic comprising the oil-based cosmetic of claim 2.

* * * * *